US012635985B2

(12) United States Patent
Kemp

(10) Patent No.: US 12,635,985 B2
(45) Date of Patent: May 26, 2026

(54) METHODS AND SYSTEMS FOR ESTABLISHING PARAMETERS FOR THREE-DIMENSIONAL IMAGING

(71) Applicant: PHILIPS IMAGE GUIDED THERAPY CORPORATION, San Diego, CA (US)

(72) Inventor: Nathaniel J. Kemp, Concord, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 19/032,850

(22) Filed: Jan. 21, 2025

(65) Prior Publication Data

US 2025/0160797 A1      May 22, 2025

Related U.S. Application Data

(63) Continuation of application No. 17/532,467, filed on Nov. 22, 2021, now Pat. No. 12,201,477, which is a continuation of application No. 14/039,106, filed on Sep. 27, 2013, now abandoned.

(60) Provisional application No. 61/710,408, filed on Oct. 5, 2012.

(51) Int. Cl.
| | |
|---|---|
| *A61B 8/12* | (2006.01) |
| *A61B 5/00* | (2006.01) |
| *A61B 8/00* | (2006.01) |
| *A61B 8/08* | (2006.01) |

(52) U.S. Cl.
CPC ............ *A61B 8/483* (2013.01); *A61B 5/0066* (2013.01); *A61B 5/0084* (2013.01); *A61B 5/6852* (2013.01); *A61B 5/748* (2013.01);

*A61B 8/12* (2013.01); *A61B 8/469* (2013.01); *A61B 8/0891* (2013.01); *A61B 8/463* (2013.01); *A61B 8/565* (2013.01)

(58) Field of Classification Search
CPC ............................... A61B 8/12; A61B 5/0084
See application file for complete search history.

(56) References Cited

U.S. PATENT DOCUMENTS

| | | | |
|---|---|---|---|
| 6,564,087 | B1 | 5/2003 | Pitris |
| 2002/0183723 | A1 | 12/2002 | Belef |

(Continued)

FOREIGN PATENT DOCUMENTS

WO      2012061940 A1      5/2012

OTHER PUBLICATIONS

Tu, et al "In Vivo Comparison of Arterial Lumen Dimensions assessed by Co-Registered three-Dimensional (3D) Quantitative Coronary Angiography, Intravascular Ultrasound and Optical Coherence Tomography", Int. Journal Cardiovascular Imaging, vol. 28, 2012, pp. 1315-1327.

(Continued)

*Primary Examiner* — Colin T. Sakamoto

(57)      ABSTRACT

The invention relates to systems and methods for the operation of three-dimensional imaging systems. Systems and methods of the invention are operable to display an image of tissue, receive a selection of points from within the image, establish a boundary corresponding to the selected points, and capture a three-dimensional image of the tissue within the designated boundary.

13 Claims, 15 Drawing Sheets

(56)  References Cited

U.S. PATENT DOCUMENTS

| | | | | |
|---|---|---|---|---|
| 2005/0119555 A1* | 6/2005 | Fritz | ................. | A61B 5/02007 600/410 |
| 2006/0058614 A1 | 3/2006 | Tsujita | | |
| 2006/0253024 A1 | 11/2006 | Altmann | | |
| 2007/0038061 A1* | 2/2007 | Huennekens | ............ | A61B 8/12 600/407 |
| 2007/0076217 A1 | 4/2007 | Baker | | |
| 2010/0249588 A1* | 9/2010 | Knight | ..................... | A61B 8/12 600/437 |
| 2011/0071404 A1* | 3/2011 | Schmitt | ................ | A61B 5/6852 382/128 |
| 2011/0071405 A1* | 3/2011 | Judell | ................ | A61B 5/02007 600/479 |
| 2012/0065511 A1* | 3/2012 | Jamello, III | ........... | A61B 8/465 600/443 |
| 2012/0075638 A1* | 3/2012 | Rollins | ................ | A61B 1/3137 356/479 |
| 2012/0130242 A1* | 5/2012 | Burgess | .................... | A61B 8/12 600/443 |
| 2012/0200845 A1 | 8/2012 | Rousseau | | |
| 2012/0215091 A1* | 8/2012 | Suzuki | ................. | G01S 15/894 600/407 |
| 2012/0253184 A1* | 10/2012 | Furuichi | ................ | A61B 5/743 600/425 |
| 2013/0079630 A1* | 3/2013 | Horiike | ................. | A61B 34/25 600/463 |

OTHER PUBLICATIONS

Tu et al "Fusion of 3D QCA and IVUS/OCT", Int. Journal Cardio-vascular Imaging, vol. 27, 2011, pp. 197-207.

* cited by examiner

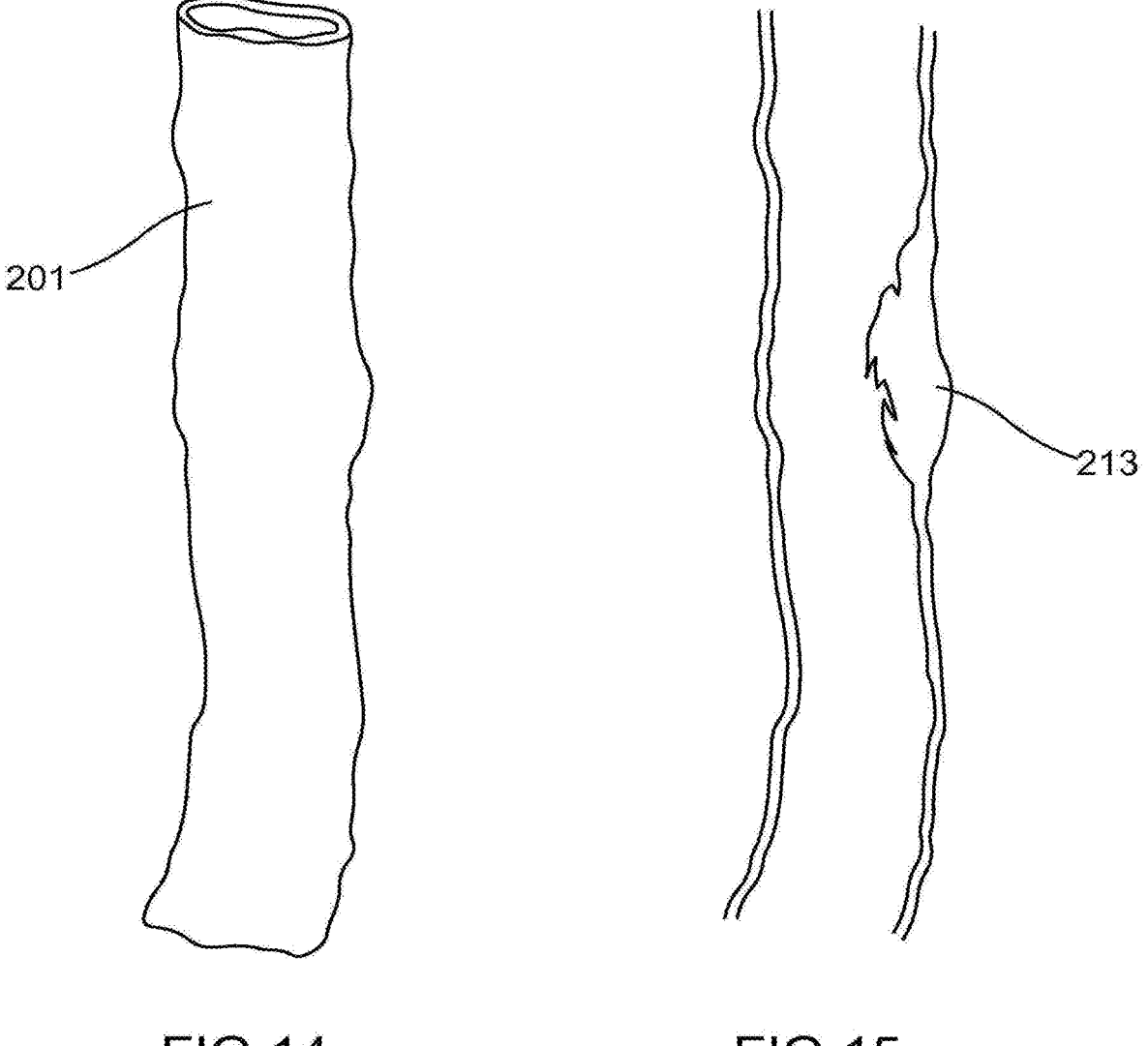
FIG.14                    FIG.15

METHODS AND SYSTEMS FOR ESTABLISHING PARAMETERS FOR THREE-DIMENSIONAL IMAGING

CROSS-REFERENCE TO RELATED APPLICATIONS

This application is a continuation of U.S. patent application Ser. No. 17/532,467, filed Nov. 22, 2021, now U.S. Pat. No. 12,201,477, which is a continuation of U.S. patent application Ser. No. 14/039,106, filed Sep. 27, 2013, which claims priority to, and the benefit of, U.S. Provisional Patent Application No. 61/710,408, filed Oct. 5, 2012, the contents of each of which are incorporated by reference.

FIELD OF THE INVENTION

The invention relates to systems and methods for the operation of three-dimensional imaging systems.

BACKGROUND

A number of technologies are available for three-dimensional imaging such as ultrasound and tomography. In medical imaging, for example, an imaging system captures an image from a patient for the analysis of bodily tissue. An physician examining such an image will sometimes recognize irregularities that indicate the presence in the tissue of a medically significant feature such as a plaque on an artery wall. To study this feature in greater detail, the physician uses the system to capture another image that focuses on the feature. To do so, the physician must input parameters to control the image capture operation, such as an indication of what region of the tissue to scan.

Programming scan parameters involves interpreting an image and either inputting numbers or mechanically driving an imaging catheter to an unseen position inside of the tissue.

For example, if a physician scans a vessel with a device that takes an image of a 10 cm range of the vessel and the resulting display reveals a region of interest near an end of the 10 cm range, the physician will study the display and determine by visual inspection approximately where within the tissue the feature is positioned. The physician then inputs numbers (e.g., 7 cm-9 cm) and triggers operation of the system to capture an image of the referenced portion of the vessel. The physician repeats these steps until the desired image is captured.

Some systems require the physician to set up a subsequent image capture operation by mechanically positioning the catheter within the tissue, for example, by repeatedly pressing a button on a handheld control module. These steps take a significant amount of time during which the catheter is resting inserted into a patient's body.

Under either approach, the physician must position the apparatus to a "best guess" position, intended to correspond to the region of interest. These methods of controlling imaging operation require the image capture parameters to be established through operations that have no inherent relationship to the tissue (mechanically driving the catheter to an unseen position or inputting numbers that represent an interpretation of the tissue). Thus, the parameter input steps are a source of inaccuracy and imprecision in the results and capturing a desired image can require expensive and time-consuming iterations and repetitions of the process.

Due to the fact that these procedures are time consuming, particularly where repeated iterations of inspection and parameter input are required, a costly amount of time is required from physicians and attendant staff. Since the parameter setting methods are imprecise, the resulting images are not optimal in that they do not always include the entire region of interest and only that region.

SUMMARY

The invention provides systems and methods for establishing control parameters for capturing a three-dimensional image of tissue. Tools of the invention allow an operator of an imaging system to select image capture parameters by interacting with a display of an image that includes a target region to be captured. By selecting image capture parameters from the displayed image, an operator generates parameters that have an inherent relationship to the tissue to be imaged. Because the image capture parameters (such as target image boundary, start and stop positions, contrast, etc.) are inherently related to the target tissue and any region of interest therein, the capture parameters are precise and accurate. Thus, systems and methods of the invention avoid expensive and time-consuming "best guess" approaches to imaging and provide a detailed and accurate image of a region of interest in tissue.

In certain aspects, the invention provides a method of imaging tissue that includes displaying a first image of the tissue and receiving a selection from within that image. The selected points are used to establish a boundary and an imaging system is operated to capture a three-dimensional image of tissue within that boundary. An imaging system can capture the image by translating an imaging device along a line, for example, by pulling or pushing a fiber optic or sonic catheter through a vessel (i.e., inside of the target tissue). An image can be captured by any means known in the art such as, for example, using sound waves or light waves. Preferably, methods and systems of the invention establish the start and stop positions for a "pullback" in an intraluminal catheter (for, e.g., OCT or IVUS). The image capture system can first capture a first image and display that to an operator, allowing the operator to make a selection. For example, where the image is displayed on a computer monitor, an operator can select pixels within the display using a computer pointing device or an element of a graphical user interface (GUI). By selecting parameters for image capture by interacting with a display that includes an image of the target tissue, parameters are established that inherently relate to the tissue being studied. For example, a region of the tissue can be chosen by mouse clicks within the display or by sliders rendered within a GUI, and that region can be used to establish a start position or stop position for a subsequent image capture operation (e.g., start and stop points for translation of an intraluminal catheter). A second three-dimensional image is captured, representing the portion of the tissue indicated by the selection. This second image can then be provided to a user, for example, by displaying it using a display device or writing a file including the image data.

In certain aspects, the invention provides an electronic device for imaging tissue that includes a non-transitory memory coupled to one or more processors and configured to display a first image of tissue. The electronic device is operable to receive a selection of points from within the first image, establish a boundary corresponding to the selected points, and capture a three-dimensional image of the tissue within the designated boundary. The electronic device captures the three dimensional image through the operation of an image capture device such as an intravascular IVUS or OCT device that operates by translating an image capture device along a line. The electronic device can receive a selection in the form of input generated via use of computer devices, such as peripheral hardware, and in which the input designates a set of pixels within the first image. The input can be generated by a user interacting with the first image, for example, in the context of a graphical user interface rendered by the electronic device. The user makes a selection of a portion of the first image and the electronic device captures a three dimensional image of the tissue for example, by starting or stopping the translation of an intravascular catheter at start point or stop point in a boundary that corresponds to part of the selection.

BRIEF DESCRIPTION OF THE DRAWINGS

FIG. 14 illustrates a portion of a vessel,

FIG. 15 is a cross-sectional view of the vessel shown in FIG. 14.

DETAILED DESCRIPTION

Figures 1, 2:
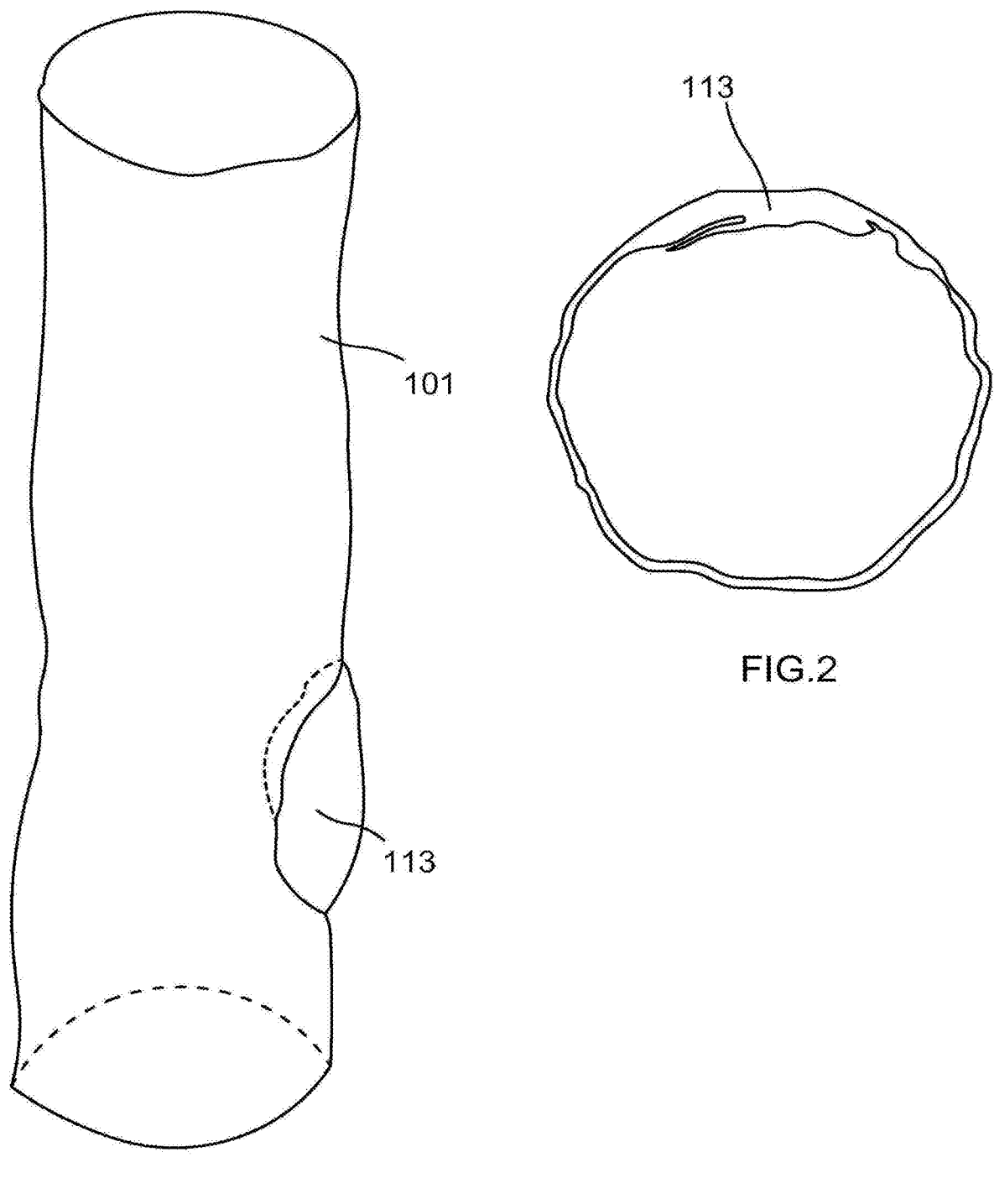
FIG. 1 is a perspective view of a vessel.
FIG. 2 is a cross-sectional view of the vessel shown in FIG. 1.

The invention provides systems and methods for setting a parameter for capturing a three-dimensional image of tissue based on an existing image. Systems and methods of the invention have application in intravascular imaging methodologies such as intravascular ultrasound (IVUS) and optical coherence tomography (OCT) among others that produce a three-dimensional image of a vessel. A segment of a vessel 101 is shown in FIG. 1 having a feature 113 of interest. FIG. 2 shows a cross-section of vessel 101 through feature 113. Intravascular imaging involves positioning an imaging device near feature 113 and collecting data representing a three-dimensional image.

Any three-dimensional imaging system may be used in systems and methods of the invention including, for example, IVUS; magnetic resonance imaging; elastographic techniques such as magnetic resonance elastography or transient elastography systems such as FibroScan by Echosens (Paris, France); electrical impedance tomography; and OCT. In certain embodiments, systems and methods of the invention include processing hardware configured to interact with more than one different three dimensional imaging system so that the tissue imaging devices and methods described here in can be alternatively used with OCT, IVUS, or other hardware.

Any target can be imaged by methods and systems of the invention including, for example, bodily tissue. In certain embodiments, systems and methods of the invention image within a lumen of tissue. Various lumen of biological structures may be imaged including, but not limited to, blood vessels, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

In an exemplary embodiment, the invention provides a system for capturing a three dimensional image by OCT. Commercially available OCT systems are employed in diverse applications such as art conservation and diagnostic medicine, e.g., ophthalmology. OCT is also used in interventional cardiology, for example, to help diagnose coronary artery disease. OCT systems and methods are described in U.S. Pub. 2011/0152771; U.S. Pub. 2010/0220334; U.S. Pub. 2009/0043191; U.S. Pub. 2008/0291463; and U.S. Pub. 2008/0180683, the contents of each of which are hereby incorporated by reference in their entirety.

In OCT, a light source delivers a beam of light to an imaging device to image target tissue. Within the light source is an optical amplifier and a tunable filter that allows a user to select a wavelength of light to be amplified. Wavelengths commonly used in medical applications include near-infrared light, for example between about 800 nm and about 1700 nm.

Generally, there are two types of OCT systems, common beam path systems and differential beam path systems, that differ from each other based upon the optical layout of the systems. A common beam path system sends all produced light through a single optical fiber to generate a reference signal and a sample signal whereas a differential beam path system splits the produced light such that a portion of the light is directed to the sample and the other portion is directed to a reference surface. Common beam path interferometers are further described for example in U.S. Pat. Nos. 7,999,938; 7,995,210; and 7,787,127, the contents of each of which are incorporated by reference herein in its entirety.

In a differential beam path system, amplified light from a light source is input into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface forming interference fringes (measured by a photovoltaic detector) allowing precise depth-resolved imaging of the target tissue on a micron scale. Exemplary differential beam path interferometers are Mach-Zehnder interferometers and Michelson interferometers. Differential beam path interferometers are further described for example in U.S. Pat. Nos. 7,783,337; 6,134,003; and 6,421,164, the contents of each of which are incorporated by reference herein in its entirety.

Figure 3:
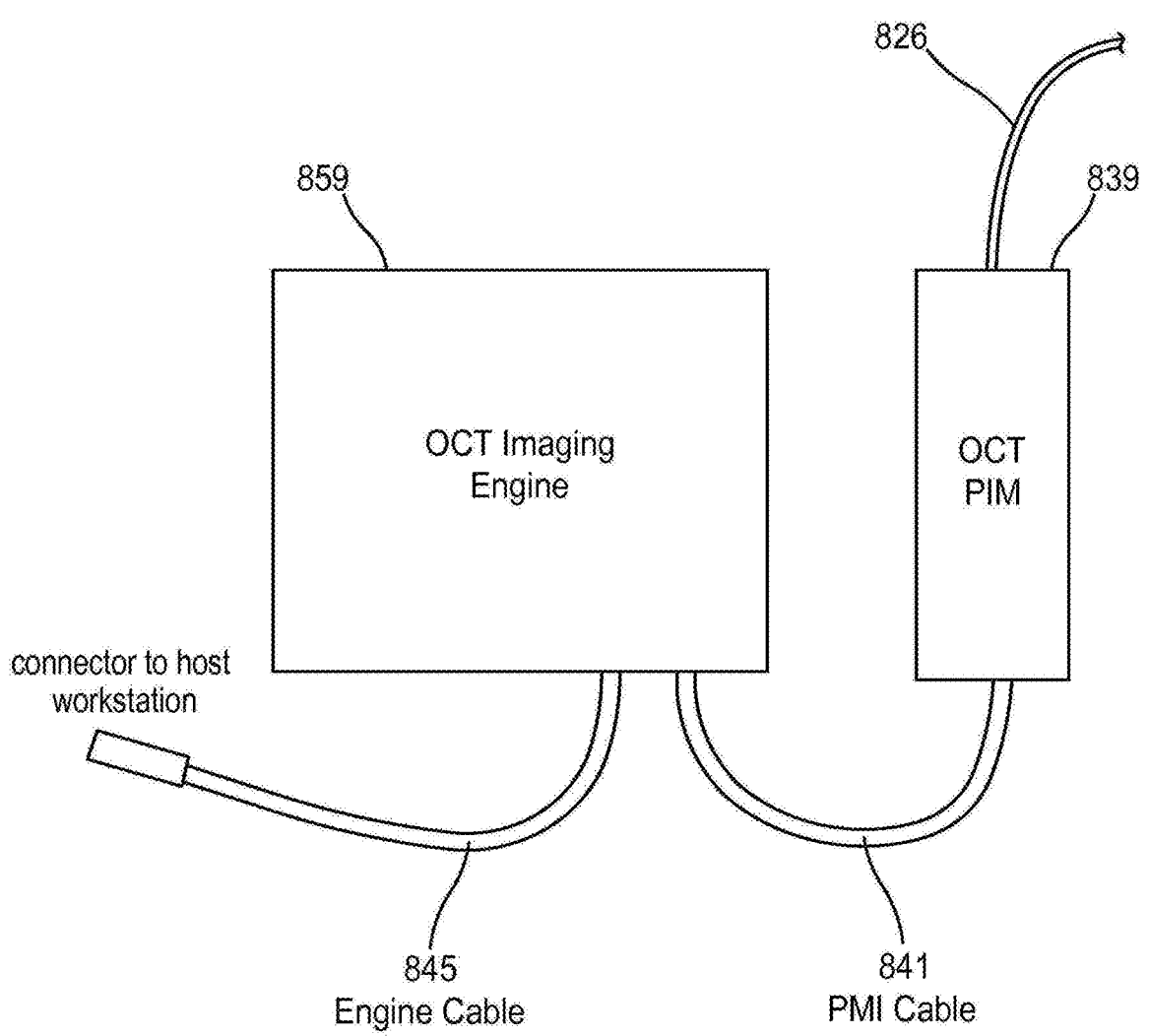
FIG. 3 is a diagram of components of an optical coherence tomography (OCT) system.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826. The imaging catheter is connected through hardware to software on a host workstation. The hardware includes an imagining engine 859 and a handheld patient interface module (PIM) 839 that includes user controls. The proximal end of the imaging catheter is connected to PIM 839, which is connected to an imaging engine as shown in FIG. 3.

Figure 4:
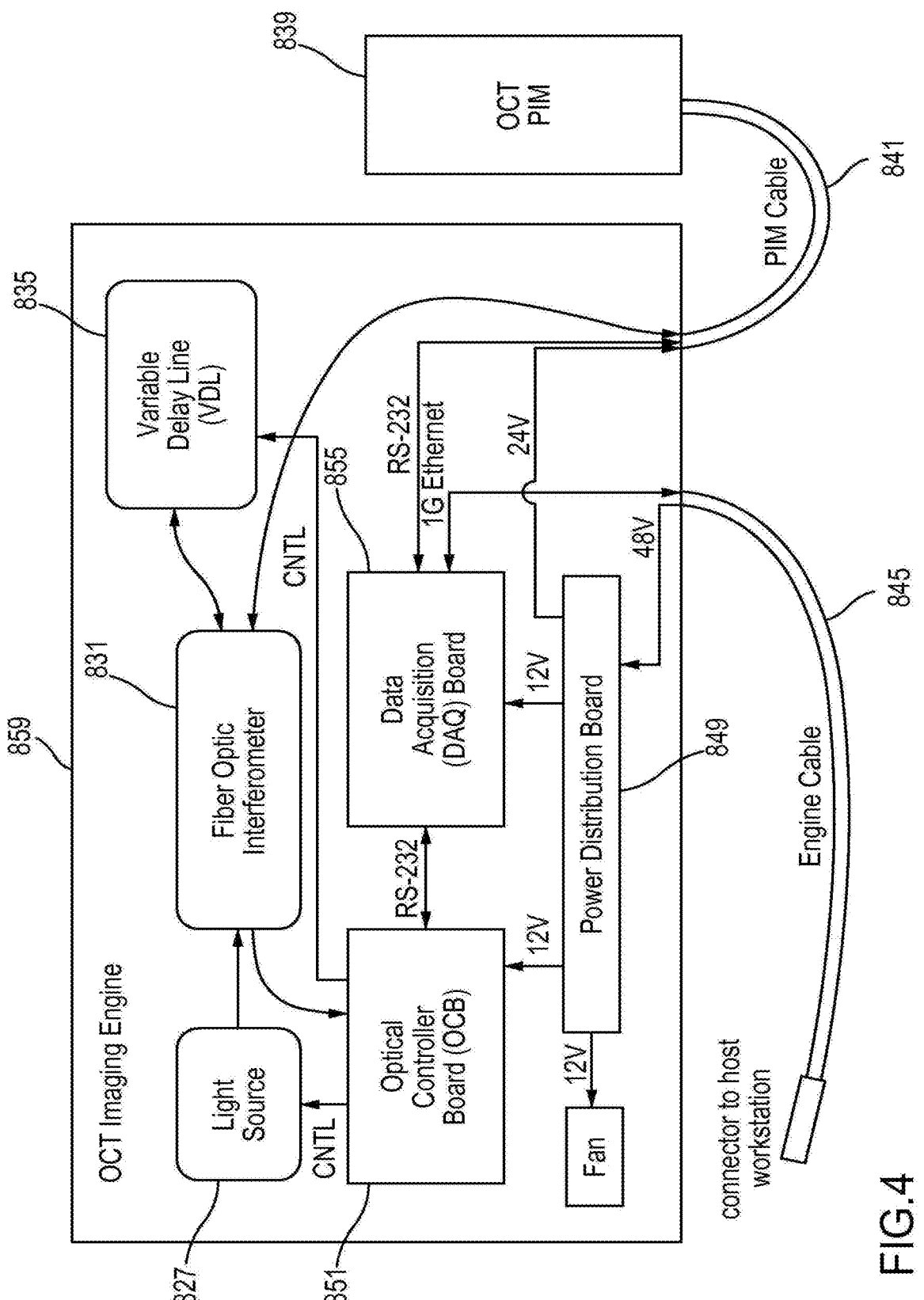
FIG. 4 is a diagram of the imaging engine shown in FIG. 3.

As shown in FIG. 4, the imaging engine 859 (e.g., a bedside unit) houses a power supply 849, light source 827, interferometer 931, and variable delay line 835 as well as a data acquisition (DAQ) board 855 and optical controller board (OCB) 854. A PIM cable 841 connects the imagine engine 859 to the PIM 839 and an engine cable 845 connects the imaging engine 859 to the host workstation.

Figure 5:
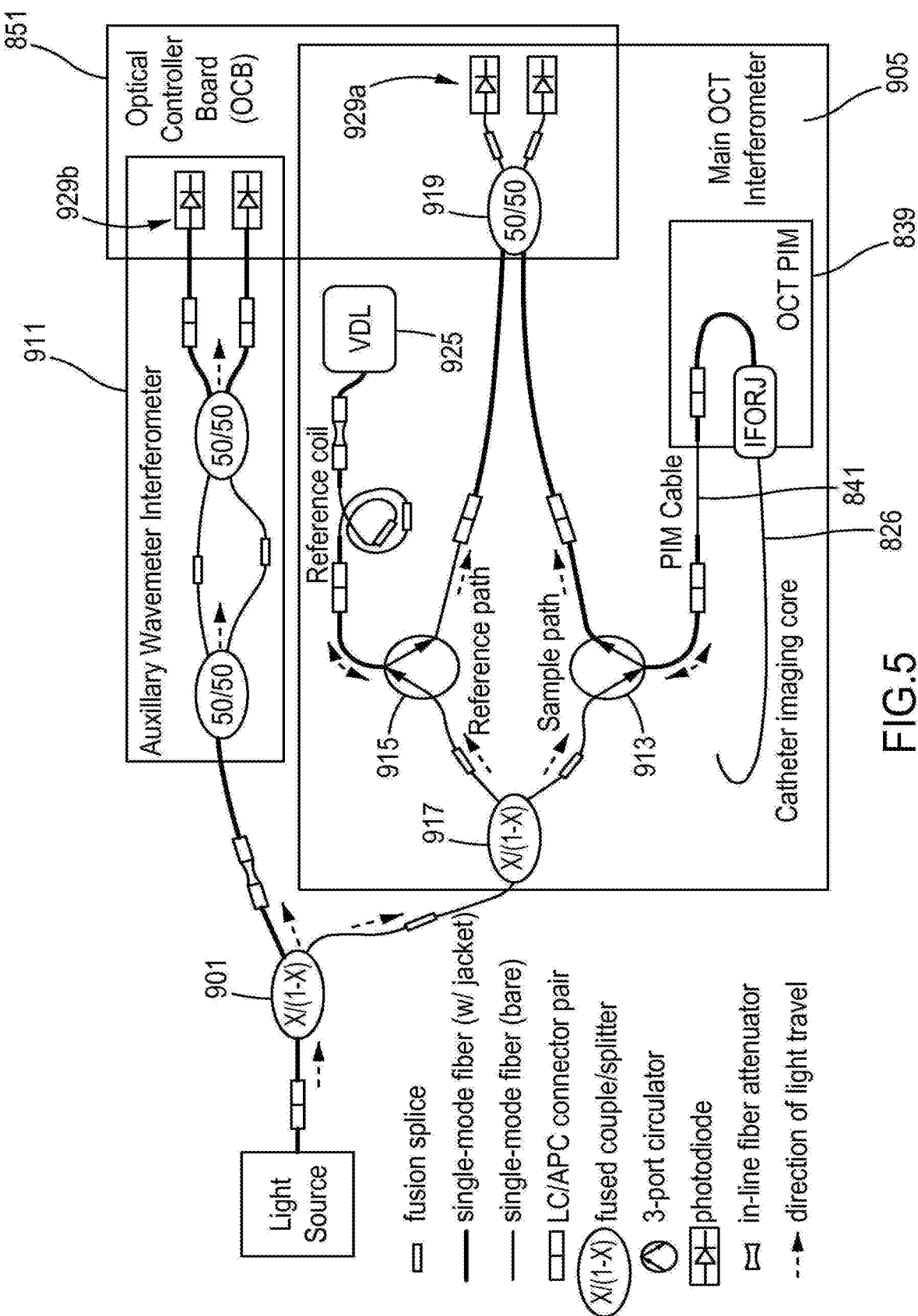
FIG. 5 is a diagram of a light path in an OCT system of certain embodiments of the invention.

FIG. 5 shows light path in a differential beam path system according to an exemplary embodiment of the invention. Light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

Figure 6:
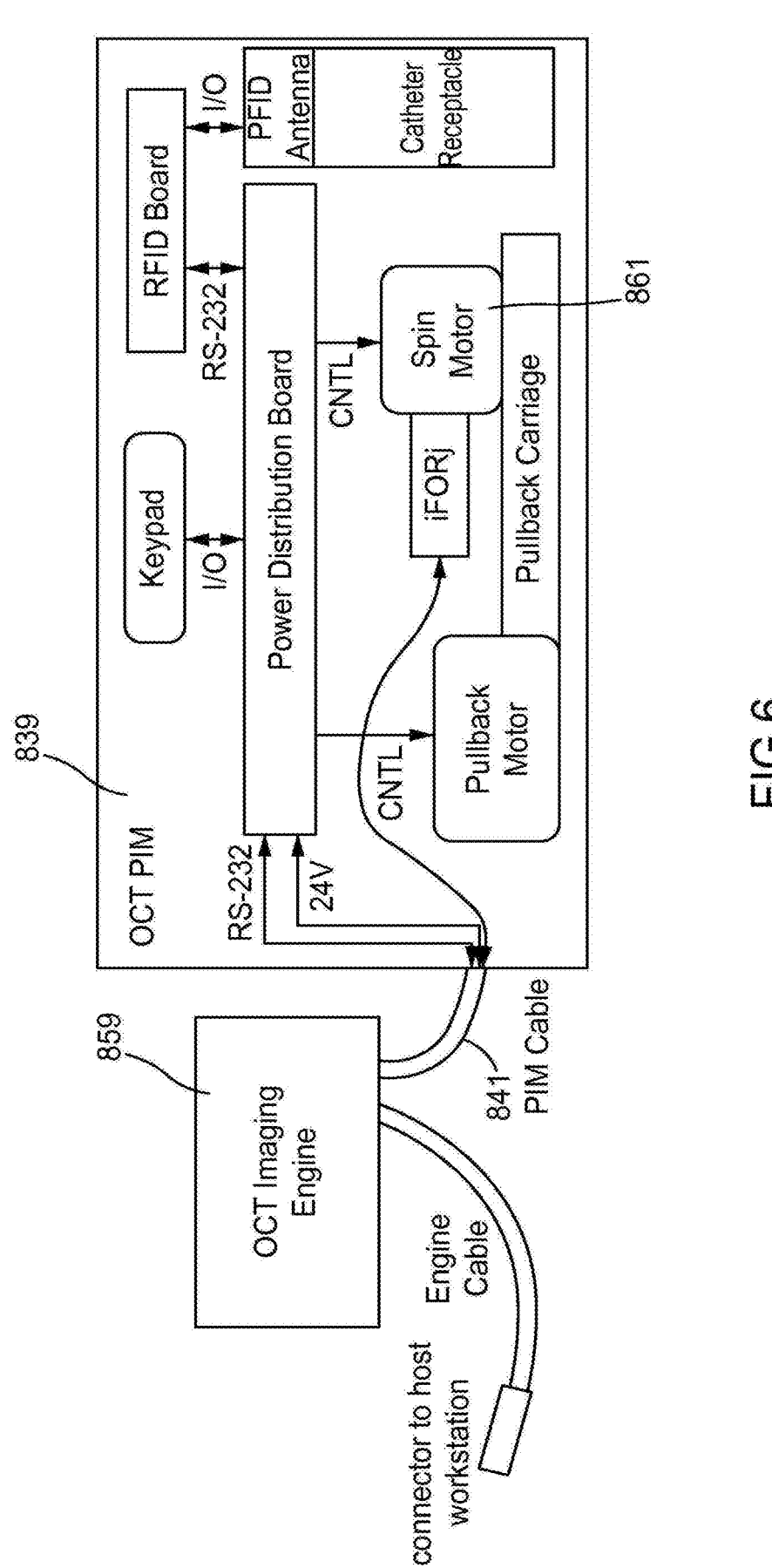
FIG. 6 is a patient interface module of an OCT system.
Figure 7:
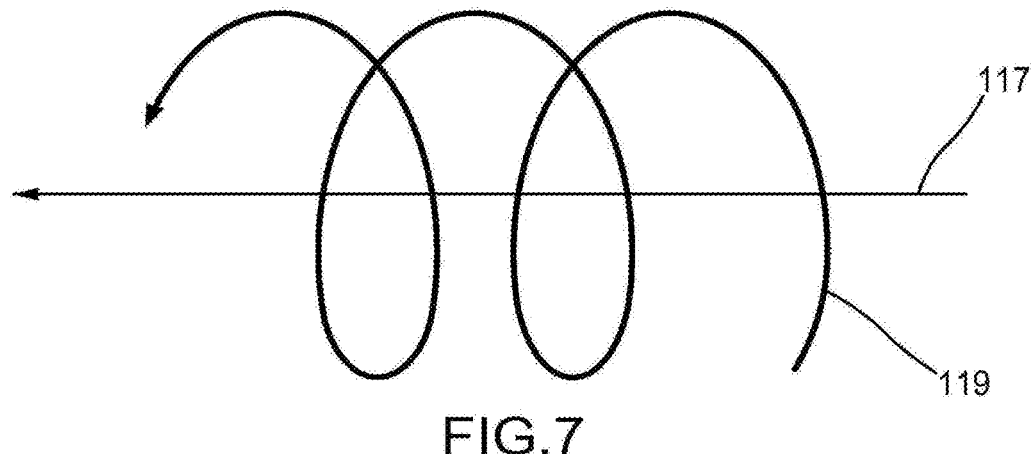
FIG. 7 is an illustration of the motion of parts of an imaging catheter according to certain embodiments of the invention.
Figure 8:
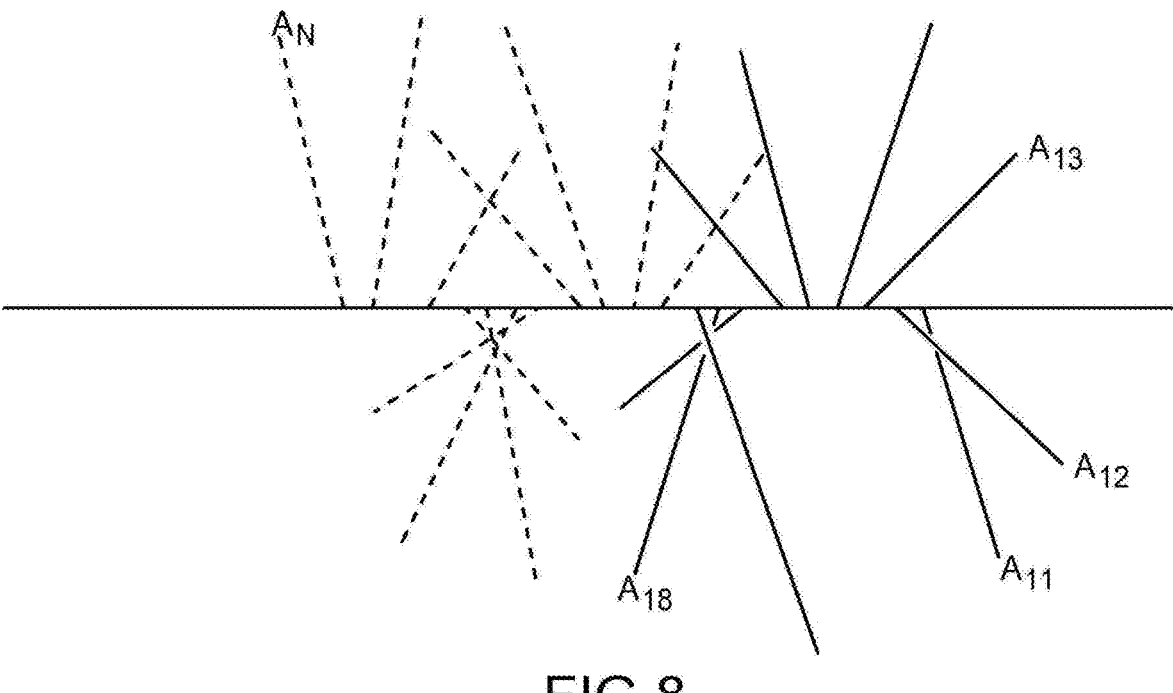
FIG. 8 shows an array of A scan lines of a three-dimensional imaging system according to certain embodiments of the invention.

Typical intravascular OCT involves introducing the imaging catheter into a patient's target vessel using standard interventional techniques and tools such as a guide wire, guide catheter, and angiography system. Rotation is driven by spin motor 861 while translation is driven by pullback motor 865, shown in FIG. 6. This results in a motion for image capture described by FIG. 7. Blood in the vessel is temporarily flushed with a clear solution for imaging. When operation is triggered from the PIM or control console, the imaging core of the catheter rotates while collecting image data that it delivers to the console screen. Using light provided by the imaging engine, the inner core sends light into the tissue in an array of A scan lines as illustrated in FIG. 8 and detects reflected light.

Figure 9:
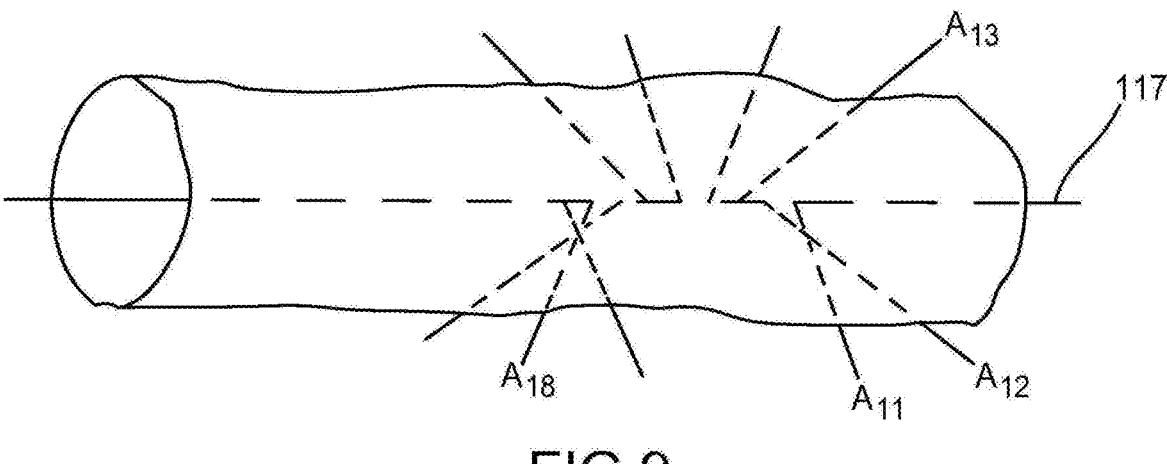
FIG. 9 shows the positioning of A scans with in a vessel.

FIG. 9 shows the positioning of A scans with in a vessel, Each place where one of A scans A11, A12, . . . , AN intersects a surface of a feature within vessel 101 (e.g., a vessel wall) coherent light is reflected and detected. Catheter 826 translates along axis 117 being pushed or pulled by pullback motor 865.

The reflected, detected light is transmitted along sample path 913 to be recombined with the light from reference path 915 at splitter 919 (FIG. 5). A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software. The free-space optical beam on the inside of the VDL 925 experiences more delay as the mirror moves away from the fixed input/output fiber.

The combined light from splitter 919 is split into orthogonal polarization states, resulting in RF-band polarization-diverse temporal interference fringe signals. The interference fringe signals are converted to photocurrents using PIN photodiodes 929a, 929b, . . . on the OCB 851 as shown in FIG. 5. The interfering, polarization splitting, and detection steps are done by a polarization diversity module (PDM) on the OCB. Signal from the OCB is sent to the DAQ 855, shown in FIG. 4. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 Gbps (e.g., compressing frames with a lossy compression JPEG encoder).

Figure 10:
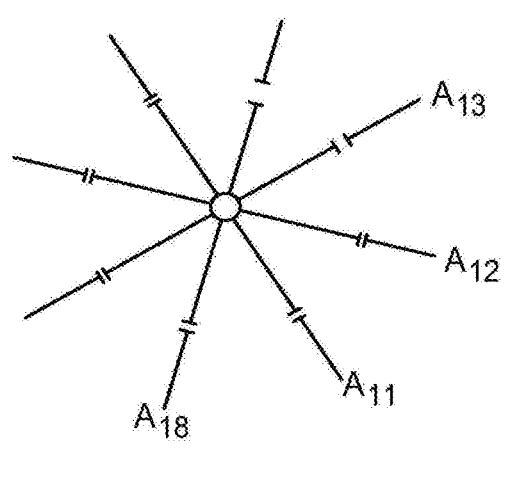
FIG. 10 illustrates a set of A scans used to compose a B scan according to certain embodiments of the invention.

Data is collected from A scans A11, A12, . . . , AN and stored in a tangible, non-transitory memory. A set of A scans generally corresponding to one rotation of catheter 826 around axis 117 collectively define a B scan. FIG. 10 illustrates a set of A scans A11, A12, . . . , A18 used to compose a B scan according to certain embodiments of the invention. These A scan lines are shown as would be seen looking down axis 117 (i.e., longitudinal distance between then is not seen).

While eight A scan lines are here illustrated, typical OCT applications can include between 300 and 1,000 A scan lines to create a B scan (e.g., about 660). Reflections detected along each A scan line are associated with features within the imaged tissue. Reflected light from each A scan is combined with corresponding light that was split and sent through reference path 915 and VDL 925 and interference between these two light paths as they are recombined indicates features in the tissue.

Figure 11:
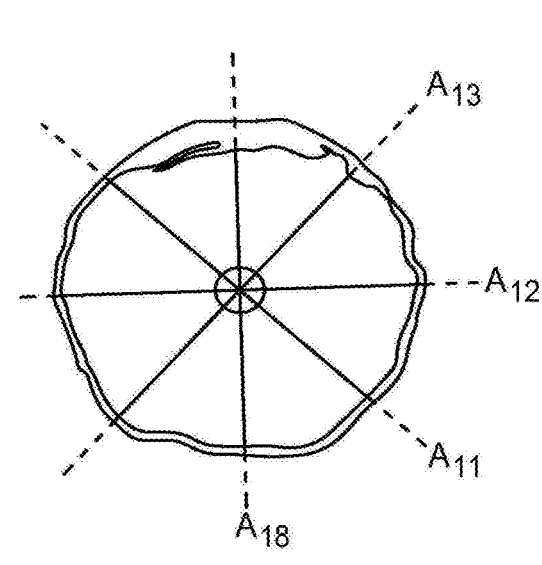
FIG. 11 shows the set of A scans shown in FIG. 10 within a cross section of a vessel.
Figure 12A:
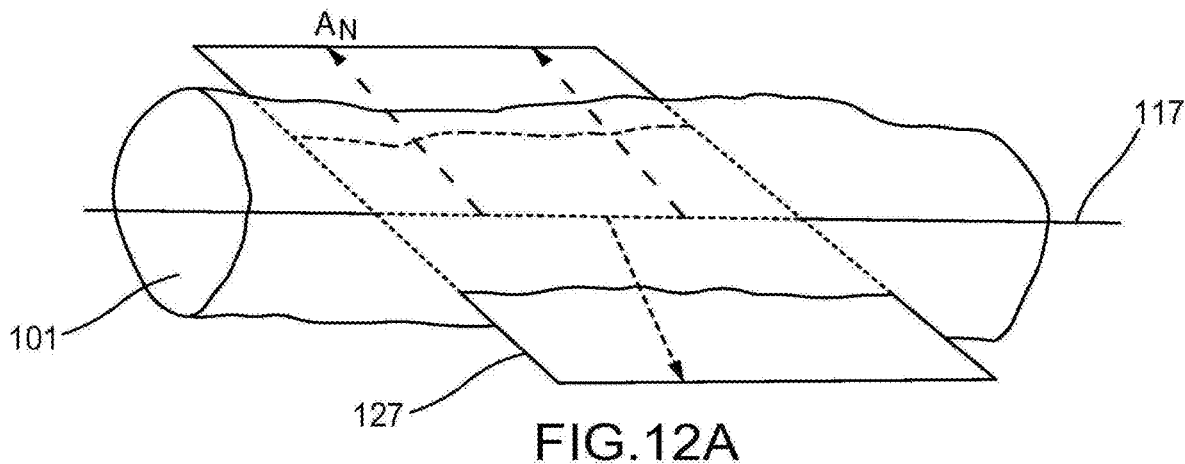
FIG. 12A shows a longitudinal plane through a vessel including several A scans.
Figure 12B:
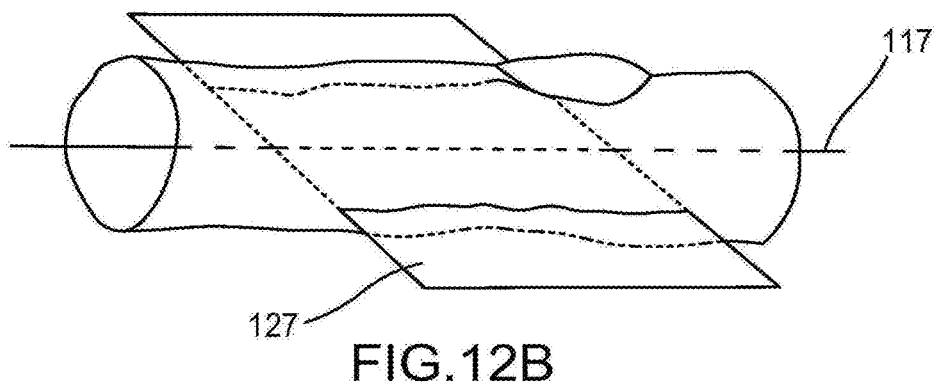
FIG. 12B shows the longitudinal plane of FIG. 12A without the A scans.

The data of all the A scan lines together represent a three-dimensional image of the tissue. The data of the A scan lines generally referred to as a B scan can be used to create an image of a cross section of the tissue, sometimes referred to as a tomographic view. For example, FIG. 11 shows the set of A scans shown in FIG. 10 within a cross section of a vessel. A B scan can be represented as a visual depiction of a cross section of a vessel (see left side of FIG. 16B).

Where a B scan generally represents an image as a planar view across a vessel or other tissue (i.e., normal to axis 117), an image can also be represented as a planar view along a vessel (i.e., axis 117 lies in the plane of the view). FIG. 12A shows a longitudinal plane 127 through a vessel 101 including several A scans. Such a planar image along a vessel is sometimes referred to as an in-line digital view or image longitudinal display (ILD). As shown in FIG. 12A, plane 127 generally comprises data associated with a subset of the A scans. FIG. 12B shows a longitudinal plane through a vessel drawn without the A scan lines to assist in visualizing plane 127 comprising axis 117.

Figure 13:
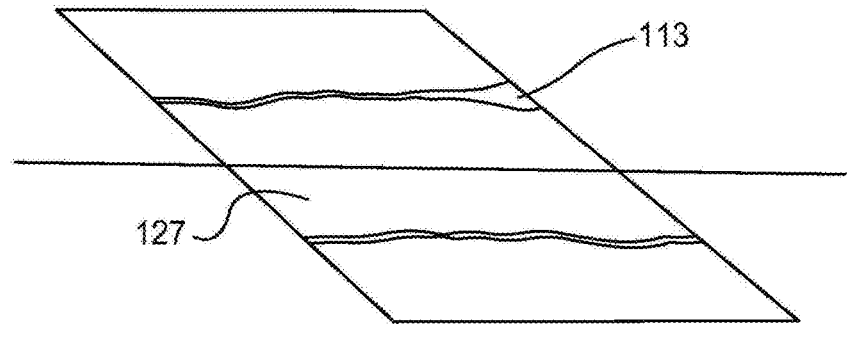
FIG. 13 is a perspective view of an image longitudinal display (ILD) in the same perspective as the longitudinal plane shown in FIGS. 12 and 12A.

The data of the A scan lines is processed according to systems and methods of the inventions to generate images of the tissue. By processing the data appropriately (e.g., by fast Fourier transformation), a two-dimensional image can be prepared from the three dimensional data set. Systems and methods of the invention provide one or more of a tomographic view, ILD, or both. FIG. 13 is a perspective view of an idealized plane shown including an exemplary ILD in the same perspective as the longitudinal plane shown in FIGS. 12 and 12A. The ILD shown in FIG. 13 can be presented by systems and methods described herein, for example, as shown in the right area of the display illustrated in FIG. 16A.

Systems and methods of the invention are operable with any compatible method of generating a three-dimensional image of tissue. In certain embodiments, the invention provides. systems and methods for imaging tissue using intravascular ultrasound (IVUS). IVUS uses a catheter with an ultrasound probe attached at the distal end. The proximal end of the catheter is attached to computerized ultrasound equipment. To visualize a vessel via IVUS, angiographic techniques are used and the physician positions the tip of a guide wire, usually 0.36 mm (0.014") diameter and about 200 cm long. The physician steers the guide wire from outside the body, through angiography catheters and into the blood vessel branch to be imaged.

The ultrasound catheter tip is slid in over the guide wire and positioned, again, using angiography techniques, so that the tip is at the farthest away position to be imaged. Sound waves are emitted from the catheter tip (e.g., in about a 20-40 MHz range) and the catheter also receives and conducts the return echo information out to the external computerized ultrasound equipment, which constructs and displays a real time ultrasound image of a thin section of the blood vessel currently surrounding the catheter tip, usually displayed at 30 frames/second image.

The guide wire is kept stationary and the ultrasound catheter tip is slid backwards, usually under motorized control at a pullback speed of 0.5 mm/s. Systems for IVUS are discussed in U.S. Pat. 5,771,895; U.S. Pub. Nos. 2009/0284332; 2009/0195514 A1; 2007/0232933; and 2005/0249391, the contents of each of which are hereby incorporated by reference in their entirety. Imaging tissue by IVUS produces tomographic (cross-sectional) or ILD images, for example, as illustrated in FIG. 16A and shown in FIG. 16B.

Systems and methods of the invention allow an operator to set an image capture parameter for three dimensional imaging. In one embodiment, systems and methods of the invention receive an image capture parameter by rendering a user interface and receiving input. via an operator's use of the interface. FIG. 14 illustrates a portion of a vessel that may be imaged and FIG. 15 is a cross-sectional view of the vessel shown in FIG. 14, presented for reference in subsequent discussion, As can be seen in FIGS. 14 and 15, example target tissue 201 includes a region of interest 213. An operator may or may not have a priori knowledge of the existence of region 213.

In certain embodiments, a system for three dimensional imaging is operated to capture an image of tissue 201. An electronic apparatus within the system (e.g., PC, dedicated hardware, or firmware) such as the host workstation 433 stores the three dimensional image in a tangible, non-transitory memory and renders a display (e.g., on a screen or computer monitor) including at least a first image of tissue 201.

Figure 16A:
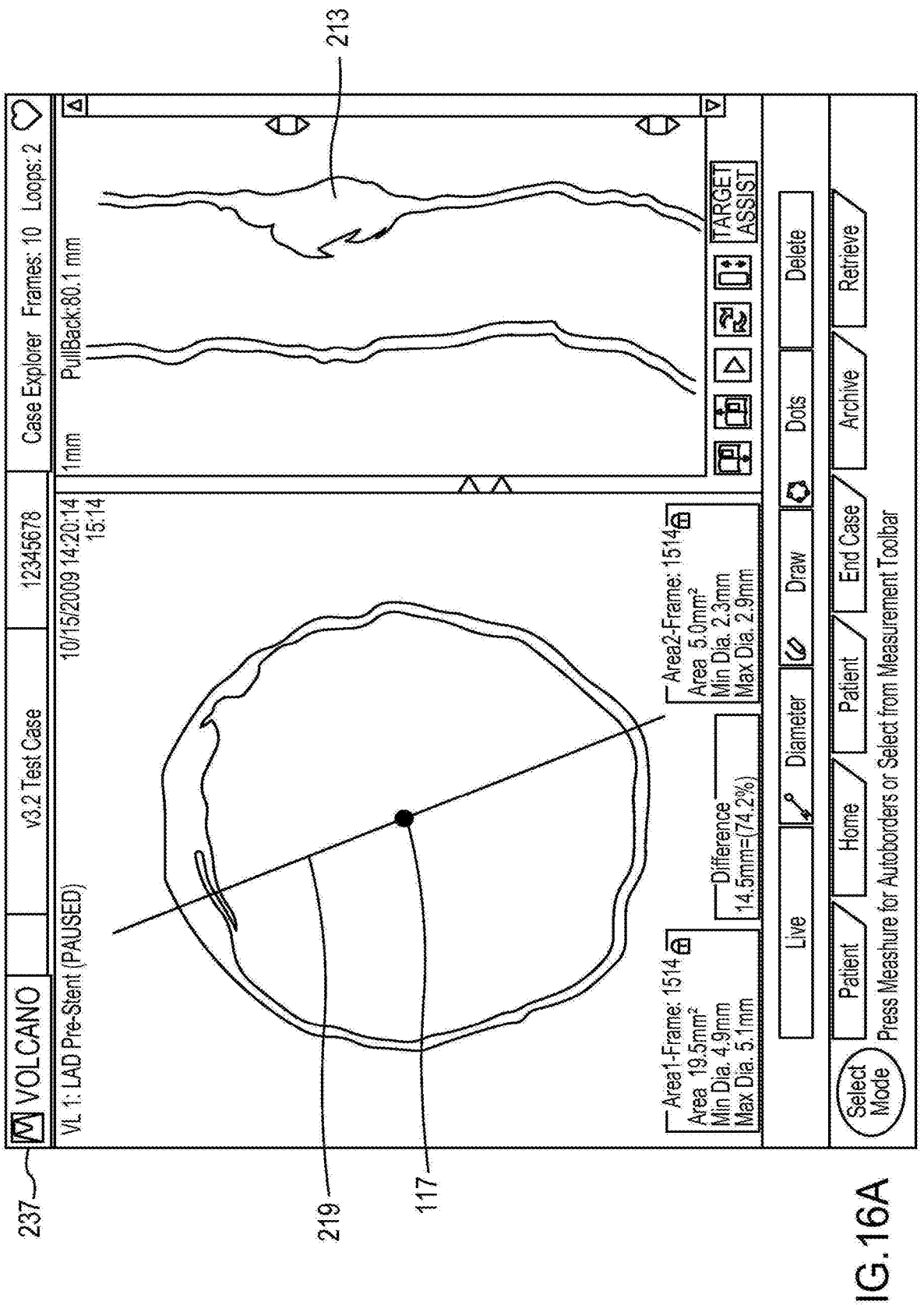
FIG. 16A is an illustration of a display including an image of the vessel shown in FIGS. 14-15.
Figure 16B:
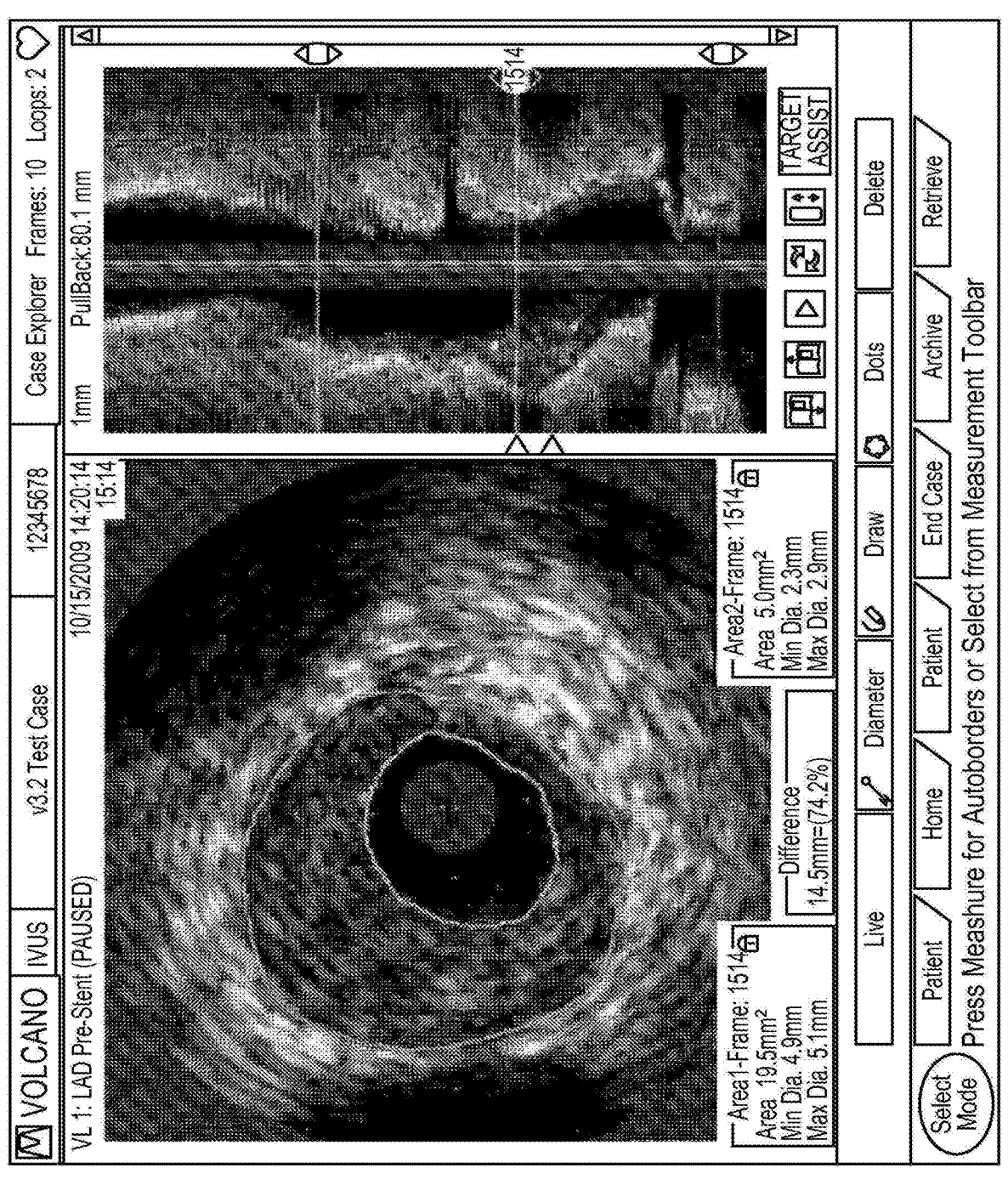
FIG. 16B shows an ultrasound display including an image of the vessel shown in FIGS. 14-15.

FIG. 16A is an illustration of a display 237 including an image of the vessel shown in FIGS. 14-15, as rendered by a system of the invention. FIG. 16B shows a display similar to that shown in FIG. 16A. The images included in display 237 in FIG. 16A are rendered in a simplified style of the purposes of ease of understanding. A system of the invention may render a display as shown in FIG. 16A, as shown in FIG. 16B, or in any style known in the art (e.g., with or without color).

In certain embodiments, display 237 is rendered within a windows-based operating system environment, such as Windows, Mac OS, or Linux or within a display or GUI of a specialized system. Display 237 can include any standard controls associated with a display (e.g., within a windowing environment) including minimize and close buttons, scroll bars, menus, and window resizing controls (not shown in FIGS. 16-19). Elements of display 237 can be provided by an operating system, windows environment, application programing interface (API), web browser, program, or combination thereof (for example, in some embodiments a computer includes an operating system in which an independent program such as a web browser runs and the independent program supplies one or more of an API to render elements of a GUI), Display 237 can further include any controls or information related to viewing images (e.g., zoom, color controls, brightness/contrast) or handling files comprising three-dimensional image data (e.g., open, save, close, select, cut, delete, etc.). Further, display 237 can include controls (e.g., buttons, sliders, tabs, switches) related to operating a three dimensional image capture system (e.g., go, stop, pause, power up, power down).

In certain embodiments, display 237 includes controls related to three dimensional imaging systems that are operable with different imaging modalities. For example, display 237 generally may include start, stop, zoom, save, etc., buttons, and be rendered by a computer program that interoperates with OCT or IVUS modalities. Thus display 237 can display an image to a user derived from a three-dimensional data set with or without regard to the imaging mode of the system.

Display 237 includes an image of tissue 201. As shown in FIG. 16A, display 237 includes two images of tissue 201, a tomographic view and an ILD. Display 237 can include indicia to show a relationship between the content of the ILD and the tomographic view such as, for example, a line 219 across the tomographic view comprising axis 117 and showing the section of tissue 201 that the ILD represents.

Systems and of the invention are configured to receive input from an operator that comprises a selection of a portion of an image in display 237. An operator may select part of an image in display 237 by any method known in the art including dragging a mouse pointer over a. portion of the display, touching a touch-sensitive screen, clicking a button to confirm a proposed selection (for example, as automatically generated by a computer program), or through interacting with one or more markers presented in display 237. The invention includes the insight that the disclosed parameter setting solves particular problems associated with intravascular imaging catheters that operate with a pullback (e.g., also with rotation) and methods and devices herein have particular benefits when used to establish start and stop positions for a pullback for an intravascular catheter such as an IVUS or OCT catheter. Such benefits include, for example, deriving value from information revealed in an ILD display while the catheter lies in the vessel ready for the next "pullback".

Figure 17:
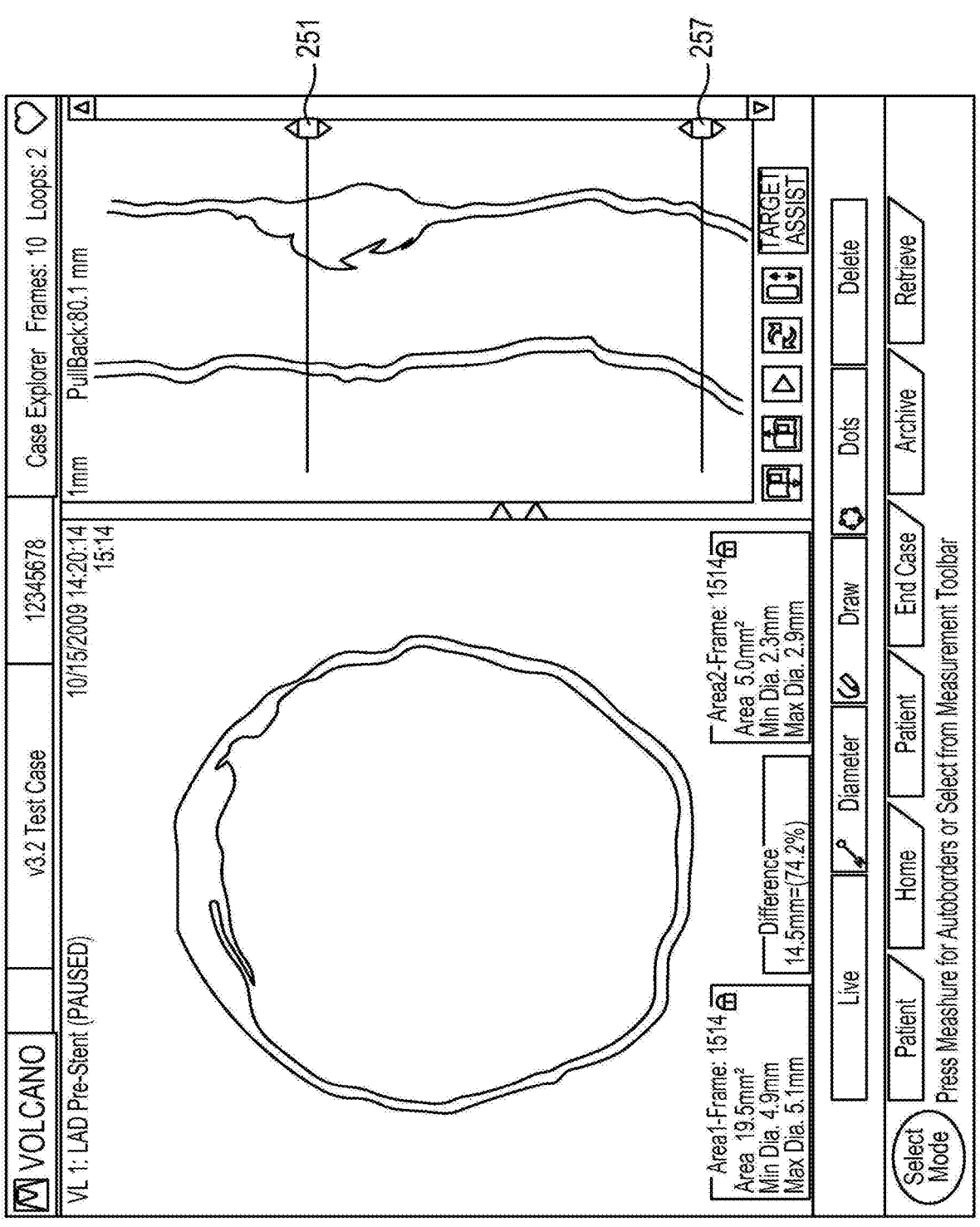
FIG. 17 is an illustration of a display including parameter-setting markers shown on the ILD.

FIG. 17 is an illustration of a display including parameter-setting markers shown on the ILD. Start marker 251 and end marker 257 can be rendered by an electronic computing device within display 237. These markers can be color-coded (e.g., green for start and red for end), animated (e.g., "marching ants" dotted line), transient (e.g., only appear when mouse pointer is hovered near certain portion of screen, or have any other quality associated with elements in a GUI. Markers can be used to mark a portion of the display and can be positioned on display 237 via an operator's interaction with a computer system (e.g., host workstation 433) including, for example, by dragging with a mouse, use of arrow keys, dragging on a touch screen or touch pad, typing in numbers, or using auto-find commands proffered by imaging software.

Figure 18:
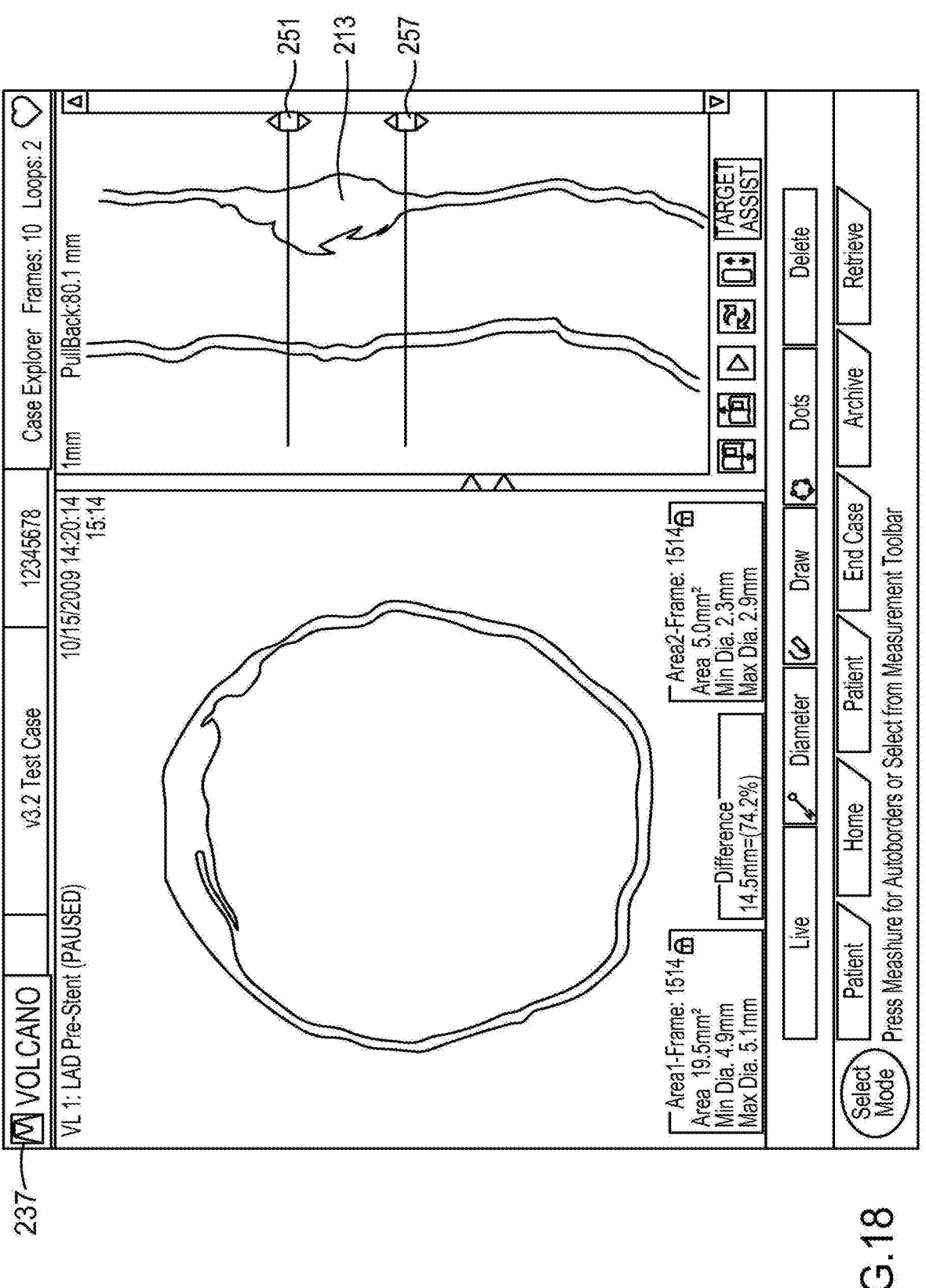
FIG. 18 is an illustration of the display shown in FIG. 17 in which the markers have been positioned to represent a selection of points within the ILD in the display.

FIG. 18 is an illustration of the display shown in FIG. 17 in which the markers have been positioned to represent a selection of points within the ILD in the display. Start marker 251 and end marker 257 generally establish a boundary defining a region of interest 213. In some embodiments, start marker 251 and end marker 257 provide tools for measuring an actual dimension of region 213. For example, where region 213 represents an adverse thrombotic feature, markers on an ILD in display 237 can be used to measure its length along vessel 201. Similar markers on a tomographic view (not shown) can be used to measure a circumferential distance of region 213. Further, similarly, markers (or mouse drag operations) can be used to measure a thickness of a feature within tissue. Since an image capture system of the invention presents display 237 based on a three dimensional data file, systems and methods of the invention can use a position of markers on a screen to calculate a dimension in three-dimensional space of the target tissue being imaged.

Systems and methods of the invention utilize a selection to establish a boundary defining a region of tissue 201. In certain embodiments, the boundary is established by a processor in an electronic device such as host workstation 433. For example, where an operator positions markers in a display at boundaries of an image of a region 213, systems of the invention can establish a corresponding boundary in three-dimensional space of the target tissue being imaged. This boundary can be calculated by a processor and stored, for example as a set of coordinates, in a tangible, non-transitory memory.

Using a boundary established based on a received selection, an image can be captured that includes region 213 and no surrounding portion of tissue 201. In certain embodiments, one image capture event, or "pullback", of an imaging system captures a fixed amount of data and imaging a smaller total area of tissue thus produces a higher level of detail, or resolution. Resolution as used herein does not strictly necessarily refer to dots or pixels per unit measurement (although that is one included exemplary definition) and is not limited to digital data but rather encompasses digital data as well as non-digital data such as light-based image data (e.g., stored on film). Resolution here refers to a level of detail or a smallest dimension of a feature that can be perceived and understood via a system or display. For a fixed quantum of input data, capturing an image of a smaller portion of tissue offers a higher resolution than capturing an image of a larger portion of the tissue. Systems of the invention capture a second image of the tissue within a designated boundary established by receiving a user selection. The user selection is made by interacting with a first image, for example, within display 237 or a GUI using techniques described herein.

In certain embodiments, an imaging system captures both the first and the second image, for example, in a single procedure. Catheter 826 is inserted into vessel 201, e.g., as described above. An operator triggers operation via PIM 839 or via a host workstation, for example, through use of a button or menu in a GUI. A three-dimensional image is captured and stored in a tangible, non-transitory medium and imaging engine 859 provides data that is rendered into a tomographic view and an ILD as shown in FIG. 17. An operator positions markers 251 and 257 at boundaries of region of interest 213 and triggers a second image capture operation. A second image is captured including only region 213 and having a higher resolution than the first image.

In certain embodiments, one or more operations or steps of an operation are performed automatically by devices or systems. Automatically generally describes an operation or step that occurs without human intervention between it and some related or causal step or operation. In certain embodiments, a boundary corresponding to a selected portion of an image (selected points) is established, a three dimensional image is captured, or both, automatically. For example, systems and methods of the invention can operate automatically and responsive to any step of operator input (e.g., a mouse release, a key stroke, a lapse of time without an input) to trigger an operation or step.

Figure 19:
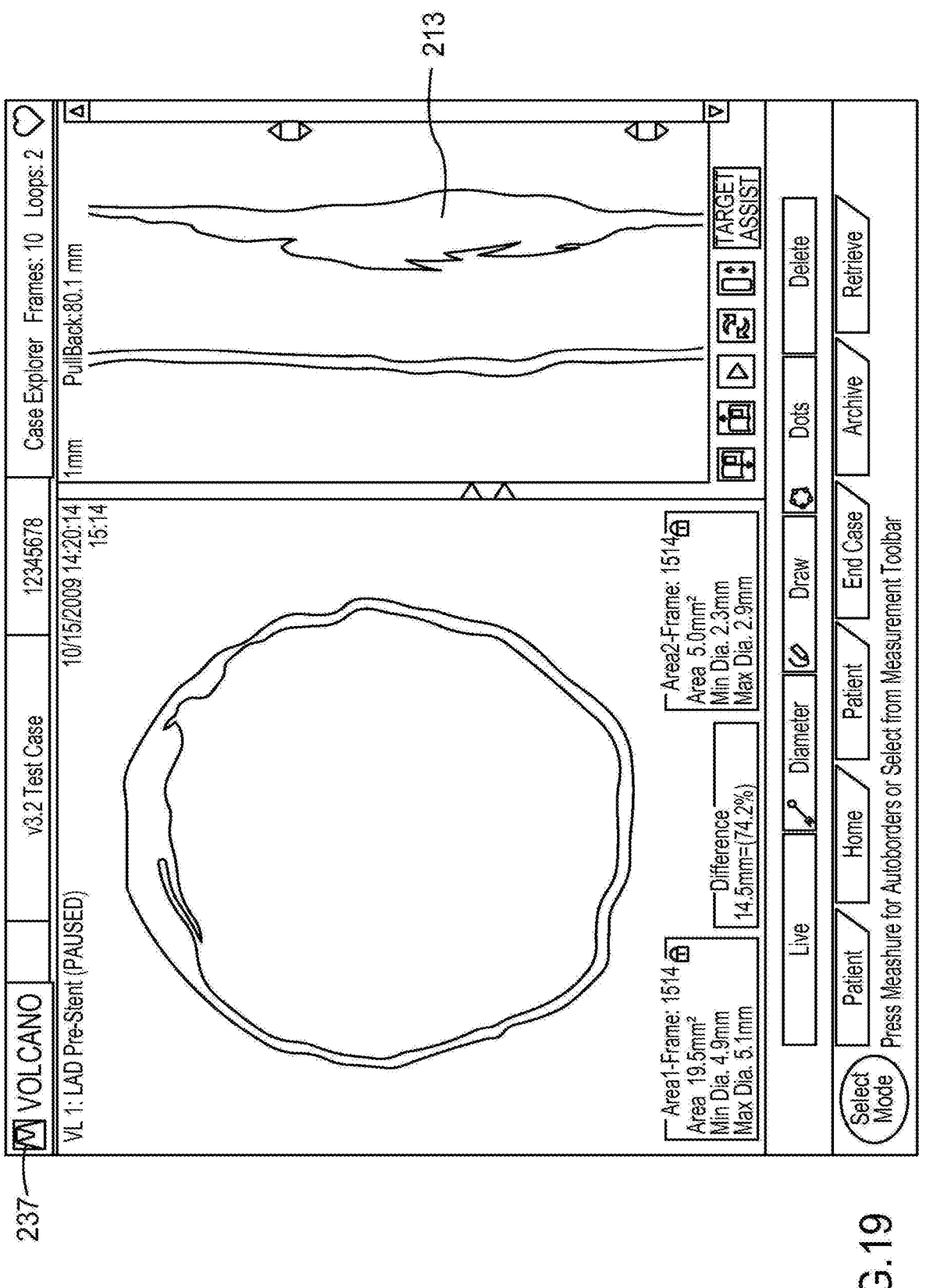
FIG. 19 is an illustration of a display including an image of the portion of the vessel corresponding to the selection represented by the position of the markers shown in FIG. 18.

FIG. 19 is an illustration of a display including a second image of the portion of the vessel corresponding to the selection represented by the position of the markers shown in FIG. 18. Here, region 213 occupies the entire ILD due to the operator's positioning of start marker 251 and end marker 257 (as seen in FIG. 18). This second ILD image and the corresponding second tomographic image (left side of display 237 in FIG. 19) are generated from the three dimensional data set generated by the imaging operation. Due to the fact that the tomographic view and the ILD each correspond to the same three dimensional target, are two dimensional views, and each represent different dimensions than the other, display 237 is said to include a three dimensional image. Furthermore, the data set from which display 237 is generated represents information in three dimensions about tissue 201.

In certain embodiments, systems of the invention render a GUI with elements or controls to allow an operator to interact with three dimensional data set as a three dimensional view. For example, an operator may cause a video affect to be viewed in, for example, a tomographic view, creating a visual effect of travelling through a lumen of vessel 201 (i.e., a dynamic progress view). Noting that a dynamic progress view (e.g., video) representing travel through a lumen of vessel 201 corresponds to a progression in a vertical direction along an ILD as shown, for example, in FIG. 17, an operator may select points from within one of the images or the three dimensional data set by choosing start and stop points while a dynamic progress view is displayed in display 237 (e.g., interact with tomographic view to choose points from within ILD).

In certain embodiments, an operator chooses a start and stop point by interacting with a tomographic view using a computer device (e.g., host workstation 433) while a dynamic progress view plays, for example, by tapping space bar for start and space bar for stop, or by clicking on the display with a mouse at moments in the dynamic progress view corresponding to start and stop points. In certain embodiments, holding down a key (e.g., "up arrow" key) causes a dynamic progress view with a "forward motion" effect and holding down another key (e.g., "down. arrow") causes a reverse motion effect. Systems of the invention can thus receive a selection of points within the first image (e.g., through interaction with the tomographic image) and optionally display start marker 251 and end marker 257 on the ILD in positions corresponding to the operator's interactions.

Certain imaging systems such as some existing OCT systems have a default 10 cm pullback length and produce images in which a default ILD represents a 10 cm length of vessel 201. Where a user selects points from within the first image corresponding to 25% of an ILD, an imaging system will then perform an image capture operation with a 2.5 cm pullback capturing an image of the target tissue as indicated by the selection. Here, in this example, the second image will have a resolution of 4× that of the first image.

While generally described here with reference to start marker 251 and end marker 257, a user may provide a selection of points within an image by interacting with any visual queue, element of a GUI, or hardware input. For example, a user may trigger operation of a plug-in or application that analyzes a first image and automatically detects an anomaly or feature and generates a selection based on the automatic detection. A user may operate an imaging system in such a way as to generate a selection based on a physical or biological phenomenon exhibited on a component of the system. For example, where pullback motor 865 generates a constant torque during a pullback, in some embodiments a system is programmed to select a region of the pullback in which the catheter travels the slowest, i.e., was subject to relatively high drag forces within the target (e.g., measured by current draw at pullback motor 865).

In certain embodiments, a user employs a macro to cause a recursive or iterative image capture operation. A macro generally refers to an operation routine including a number of steps preferably programmed to run automatically once triggered. For example, a user may designate a single point within an ILD and cause the system to capture the 10% of the ILD surrounding the point, display the high resolution second image, capture the 10% of the second ILD surrounding the same point, display the higher still resolution third image, and so on, for any number of cycles (recursive model). In an iterative model, a user my select a region of a first image (e.g., 10% of the ILD) and cause a system to perform one image capture operation of the first 10% of the selection (i.e., 1% of the first ILD), one image capture operation of the second 10% of the selection, . . . and so on, until the first selected region has been imaged by 10 pull-backs creating a final image with 100× resolution compared to the first image.

In certain embodiments, start marker 251 and end marker 257 operate as rulers to measure a dimension or to control video playback while also operating as a mechanism by which an operator inputs a selection. Thus, an operator may examine a first image in dynamic progress view or in any other video-type playback mode and use the markers to establish parameters of the video. The operator may then confirm to the system that the markers also represent the selection to be used to establish a boundary for a subsequent image capture operation. Note that this process can proceed iteratively. An operator can view the second image in dynamic progress view, for example, and again choose a target region for a third imaging operation, and so on.

Figure 20:
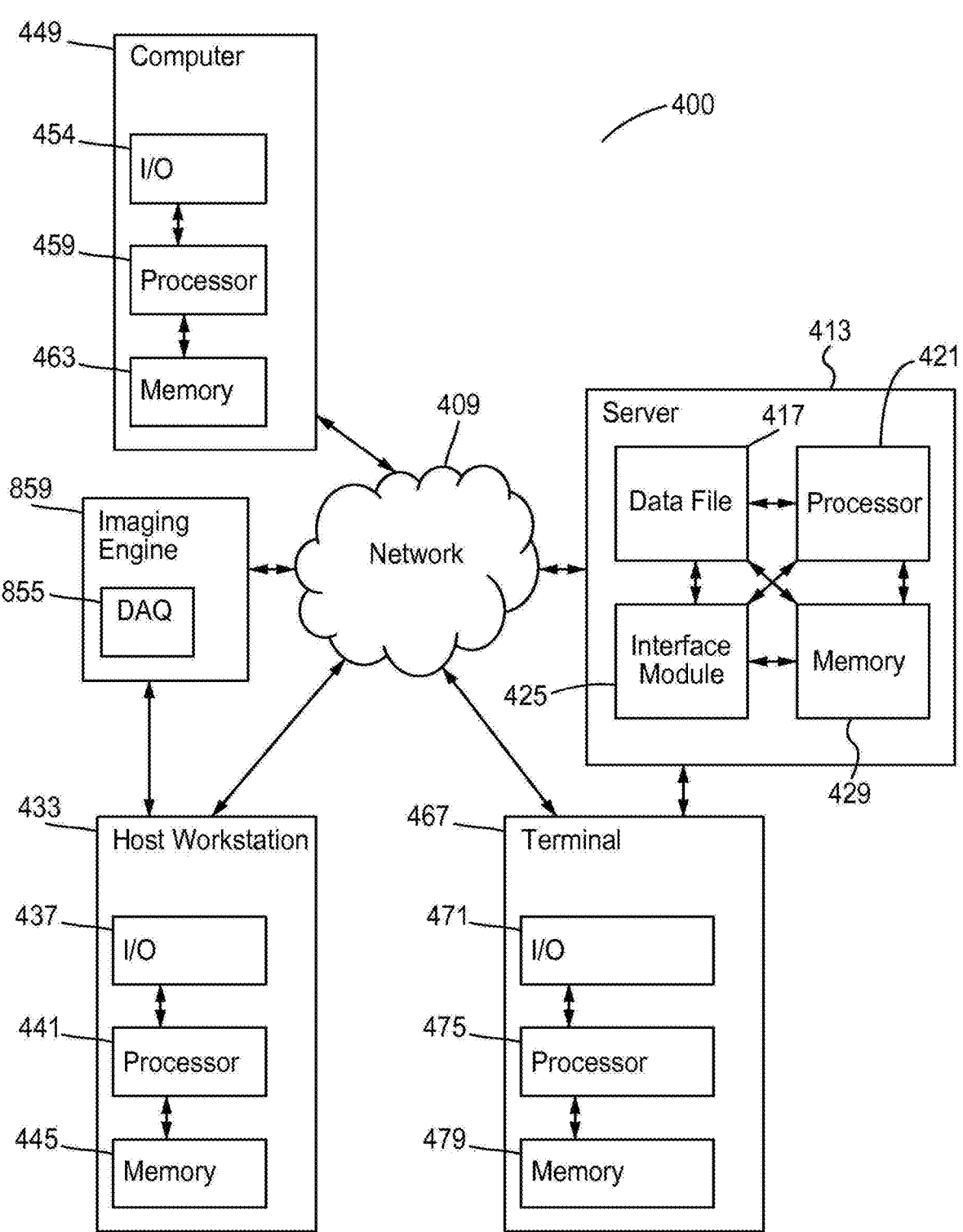
FIG. 20 is a system diagram according to certain embodiments.

In some embodiments, a user interacts with a visual interface and puts in parameters or makes a selection. Input from a user (e.g., parameters or a selection) are received by a processor in an electronic device such as, for example, host workstation 433, server 413, or computer 449. The selection can be rendered into a visible display. An exemplary system including an electronic device is illustrated in FIG. 20. As shown in FIG. 20, imaging engine 859 communicates with host workstation 433 as well as optionally server 413 over network 409. In some embodiments, an operator uses host workstation 433, computer 449, or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417. Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate build-ings, for example, with wireless or wired connections). In certain embodiments, host workstation 433 and imaging engine 855 are included in a bedside console unit to operate system 400.

Processors suitable for the execution of computer pro-gram include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more non-transitory memory devices for storing instruc-tions and data. Generally, a computer will also include, or be operatively coupled to receive data from or transfer data to, or both, one or more mass storage devices for storing data, e.g., magnetic, magneto-optical disks, or optical disks. Infor-mation carriers suitable for embodying computer program instructions and data include all forms of non-volatile, tangible, non-transitory memory, including by way of example semiconductor memory devices, (e.g., EPROM, EEPROM, NAND-based flash memory, solid state drive (SSD), and other flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an imple-mentation of the subject matter described herein), or any combination of such back-end, middleware, and front-end components. The components of the system can be inter-connected through network 409 by any form or medium of digital data communication, e.g., a communication network. Examples of communication networks include cell networks (3G, 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment) into patterns of magnetization by read/write heads, the patterns then representing new collocations of information desired by, and useful to, the user. In some embodiments, writing involves a physical transformation of material in tangible, non-transitory computer readable media with certain properties so that optical read/write devices can then read the new and useful collocation of information (e.g., burning a CD-ROM). In some embodiments, writing a file includes using flash memory such as NAND flash memory and storing information in an array of memory cells include floating-gate transistors. Methods of writing a file are well-known in the art and, for example, can be invoked automatically by a program or by a save command from software or a write command from a programming language.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:
1. A system, comprising:
an intravascular imaging catheter configured to obtain intravascular imaging data while the intravascular imaging catheter is positioned inside a blood vessel; and
a processor configured for communication with the intravascular imaging catheter, wherein the processor is configured to:
control the intravascular imaging catheter to obtain the intravascular imaging data;
generate, using the intravascular imaging data, a two-dimensional (2D) longitudinal cross-sectional view of the blood vessel representative of a length of the blood vessel;
output, to a display in communication with the processor, a screen display comprising:
the 2D longitudinal cross-sectional view, wherein the 2D longitudinal cross-sectional view comprises a first long edge and an opposite, second long edge, wherein the first and second long edges are oriented along the length of the blood vessel; and
a first marker and a second marker overlaid on the 2D longitudinal cross-sectional view and defining a region of interest of the blood vessel, wherein each marker of the first marker and the second marker comprises:
a slider located on the first long edge; and
an indicator extending between the slider and the second long edge such that the indicator is oriented perpendicular to the length of the blood vessel and the indicator is positioned across the blood vessel in the 2D longitudinal cross-sectional view;
receive a user input to independently move the first marker relative the second marker to a new location such that the user input comprises a manual change to a length of the region of interest; and
update the screen display based on the user input such that the first marker is overlaid on the 2D longitudinal cross-sectional view in the new location.
2. The system of claim 1, wherein the first marker and the second marker indicate a beginning and an end of the length of the region of interest.
3. The system of claim 1, wherein the region of interest comprises an adverse thrombotic feature.
4. The system of claim 1, wherein the intravascular imaging data comprises three-dimensional imaging data.
5. The system of claim 1,
wherein the intravascular imaging catheter comprises an image capture device, and
wherein the intravascular imaging catheter is configured to obtain the intravascular imaging data using the image capture device.
6. The system of claim 1, wherein the intravascular imaging data is obtained with sound waves or light waves.
7. The system of claim 1, wherein the processor is configured to generate, using the intravascular imaging data, a plurality of 2D cross-sectional views of the blood vessel.
8. The system of claim 7, wherein the screen display comprises a 2D cross-sectional view of the plurality of 2D cross-sectional views.

9. The system of claim 8, wherein the 2D cross-sectional view and the 2D longitudinal cross-sectional view are simultaneously displayed in the screen display.

10. The system of claim 1, wherein the processor is configured to measure the length of the region of interest based on the first marker and the second marker.

11. The system of claim 1, wherein the processor is configured to receive the user input via a touchscreen.

12. The system of claim 1, wherein, to control the intravascular imaging catheter, the processor is configured to control a pullback of the intravascular imaging catheter through the blood vessel.

13. The system of claim 1, wherein the indicator is centered relative to the slider.

\* \* \* \* \*